(12) United States Patent
Binder et al.

(10) Patent No.: US 6,582,939 B1
(45) Date of Patent: Jun. 24, 2003

(54) PROCESS FOR THE PREPARATION OF ALKALINE EARTH SALTS OF D-PANTOTHENIC ACID

(75) Inventors: Michael Binder, Steinhagen (DE); Walter Pfefferle, Halle (Westf.) (DE); Ulrich Becker, Borgholzhausen (DE); Ilona Walger, Bielefeld (DE); Klaus Erich Uffmann, Bielefeld (DE); Georg Thierbach, Bielefeld (DE); Achim Marx, Bielefeld (DE); Thomas Hermann, Bielefeld (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/686,170

(22) Filed: Oct. 12, 2000

(30) Foreign Application Priority Data

May 3, 2000 (DE) .......................................... 100 21 515

(51) Int. Cl.⁷ ................................................ C12P 13/04
(52) U.S. Cl. ...................... 435/106; 435/116; 435/146; 435/244
(58) Field of Search ................................ 435/106, 116, 435/146, 244

(56) References Cited

U.S. PATENT DOCUMENTS

| 5,518,906 A | * | 5/1996 | Hikichi et al. ............... 435/116 |
| 5,932,457 A | * | 8/1999 | Moriya et al. ............... 435/146 |

FOREIGN PATENT DOCUMENTS

| EP | 0 493 060 | 7/1992 |
| EP | 0 590 857 | 4/1994 |
| GB | 683 423 | 11/1952 |
| WO | WO 97 10 340 | 3/1997 |

OTHER PUBLICATIONS

Cronan et al "Gene and Biochemical Analyses of Pantothenate Biosynthesis in *Escherichia coli* in", J. Bacter. 149(3):916–922 (Mar. 1982).*

* cited by examiner

*Primary Examiner*—Irene Marx
(74) *Attorney, Agent, or Firm*—Pillsbury Winthrop LLP

(57) ABSTRACT

The preparation of alkaline earth salts of D-pantothenic acid, in which the fermentation is carried out in the presence of alkaline earth compounds.

9 Claims, No Drawings

PROCESS FOR THE PREPARATION OF ALKALINE EARTH SALTS OF D-PANTOTHENIC ACID

CROSS-REFERENCE TO RELATED APPLICATION

This application is based on German Application DE 100 21 515.7, filed May 3, 2000, which disclosure is incorporated herein by reference.

FIELD OF THE INVENTION

The present invention relates to a process for the preparation of alkaline earth salts of D-pantothenic acid from fermentation broths.

BACKGROUND OF THE INVENTION

Pantothenic acid is a commercially important vitamin that is used in cosmetics, medicine, human nutrition and in animal nutrition.

Pantothenic acid can be prepared by chemical synthesis or via biotechnology by fermentation of suitable microorganisms in suitable nutrient solutions. DL-pantolactone is an important compound in the chemical synthesis, and is prepared in a multi-stage process from formaldehyde, isobutyl aldehyde and cyanide. In further process steps the racemic mixture is separated and D-pantolactone is condensed with β-alanine to yield D-pantothenic acid.

The advantage of a fermentative preparation using microorganisms is the direct formation of the correct stereoisometric form, namely the D-form of pantothenic acid free from L-pantothenic acid.

Various types of bacteria, for example *Escherichia coli*, *Arthrobacter ureafaciens*, *Corynebacterium erythrogenes*, *Brevibacterium ammoniagenes* and also yeasts, for example Debaromyces castellii may, as demonstrated in EP-A-0 493 060, EP-A-0 590 857 and WO 97/10340, produce D-pantothenic acid under suitable fermentation conditions. Particularly suitable microorganisms are the derivatives, described in the citations, of *Escherichia coli* IF03547, for example the strains FV5069/pFV31 or FV5069/pFV202.

In the fermentative preparation of D-pantothenic acid as is described in EP-A-0 493 060, EP-A-0 590 857 and WO 97/10340, a microorganism capable of producing D-pantothenic acid is cultivated in a suitable nutrient medium and the D-pantothenic acid that is formed is then isolated according to a complicated expensive procedure, purified, and obtained as the calcium salt.

Suitable nutrient media contain a carbon source such as glucose or starch flour hydrolyzate, precursors such as β-alanine, D,L-pantoic acid or D,L-pantolactone, a nitrogen source such as ammonium sulfate, a phosphorus source such as potassium phosphate, and further salts, trace elements, amino acids and vitamins, and optionally complex media additives such as yeast extract or corn steep liquor. The microorganisms are then incubated in this medium at a suitable pH value under appropriate aeration and stirring, whereupon the microorganisms form D-pantothenic acid.

EP-A-0 590 857 describes, for example, a fed batch process for preparing pantothenic acid in a 5 liter reactor filled with 2.3 liter or 2.5 liter of culture medium. In this experimental example, solid calcium carbonate was added presumably to regulate the pH. The preliminary addition or subsequent addition of solid calcium carbonate is however extremely undesirable in a large-scale reactor having a volume of many cubic meters, because the material loading is increased by the calcium carbonate deposits on the stirrer blades, internal surfaces and seals, and the flow properties of the culture liquid and the sterile conditions are adversely affected.

According to the present prior art, which is outlined in W096/33283 and EP-A-0 590857, the calcium salt of D-pantothenic acid is obtained by a complicated and costly isolation and purification process starting from a fermentation broth containing pantothenic acid. After a first separation of the biomass by filtration or centrifugation, the filtrate is worked up further by purification by means of activated charcoal or by column chromatography. After adding calcium hydroxide to the pretreated filtrate or eluate, the batch is then purified by crystallization.

The purification method described in W096/33283 is carried out as follows. The filtrate is decolorized by means of activated charcoal in a first column. The pH is adjusted to 3.0 with concentrated hydrochloric acid and the liquid is then purified continuously through two columns packed with activated charcoal. The elution of the D-pantothenic acid is performed with methyl alcohol. A subsequent neutralization is carried out with $Ca(OH)_2$ powder while thoroughly mixing. The calcium D-pantothenate is obtained by subsequent crystallization at 5° C.

The purification method described in EP-A 0 590 857 is carried out as follows. The filtrate is first of all purified with the aid of cation exchange and anion exchange columns. Elution is performed with hydrochloric acid. The eluted fraction is then neutralized with $Ca(OH)_2$, following which activated charcoal is added and the mixture is filtered. The resultant filtrate is extracted in a low molecular weight alcohol (methanol, ethanol, isopropanol) and the calcium D-pantothenate is obtained by crystallization.

The calcium D-pantothenate prepared in the aforementioned manner is used as a feed additive for animal nutrition.

SUMMARY OF THE INVENTION

An improved process for preparing alkaline earth salts, in particular the calcium and magnesium salts, of D-pantothenic acid, which are suitable for use as feed additives in animal nutrition, is provided.

The vitamin D-pantothenic acid is a commercially important product that is used in animal nutrition, medicine, human nutrition and in cosmetics. There is, therefore, a general interest in providing new processes for preparing pantothenic acid or its salts.

The present invention provides a process for preparing alkaline earth salts of D-pantothenic acid or mixtures containing the latter, from fermentation broths, which is characterized in that
  (a) the fermentation is carried out in the presence of alkaline earth compound,
  (b) after completion of the fermentation the biomass is optionally removed either in whole or in part,
  (c) the thus worked up fermentation broth is concentrated, and
  (d) the alkaline earth salt or salts of D-pantothenic acid is/are obtained from the latter in pure form or as a mixture containing the constituents of the fermentation broth.

The present invention also provides a process which is characterized in that one or more alkaline earth salt(s) of D-pantothenic acid is/are added in the desired amount to the constituents of the fermentation broth and mixture containing one or more of the alkaline earth salts of D-pantothenic acid.

The invention furthermore provides a process for preparing alkaline earth salts of D-pantothenic acid, characterized in that
a) the biomass is separated from a fermentation broth containing alkaline earth salt(s) of D-pantothenic acid,
b) the cell-free fermentation broth is concentrated,
c) a hydrophilic organic solvent, in particular ethanol, methanol or acetone, is added to the concentrate thus obtained, following which
d) the alkaline earth salt(s) of pantothenic acid is/are isolated, optionally washed with a hydrophilic organic solvent and then, if desired,
e) recrystallized in an aqueous solution of a hydrophilic organic solvent, optionally with the addition of activated charcoal, and obtained in a high state of purity.

All microorganisms that are capable of producing D-pantothenic acid and which produce D-pantothenic acid under appropriate fermentation conditions are suitable for the process according to the invention. The microorganisms can produce pantothenic acid from glucose, sucrose, lactose, fructose, maltose, molasses, starch, cellulose or from glycerol and ethanol.

The microorganisms may be fungi or yeasts, for example *Debaromyces castells* or *Saccharomyces cerevisiae* or Gram-positive bacteria, for example of the genus Corynebacterium or may be Gram-negative bacteria, for example of the family of Enterobacteriaceae. Within the family of Enterobacteriaceae, the genus Escherichia as exemplified by the type *Escherichia coli*, in particular, should be mentioned. Within the type *Escherichia coli* there should be mentioned the so-called K-12 strains, for example the strains MG1655 or W3110 (Neidhard et al.: *Escherichia coli* and Salmonella. Cellular and Molecular Biology (ASM Press, Washington D.C.)) or the *Escherichia coli* wild type strain IF03547 (Institute for Fermentation, Osaka, Japan) and mutants derived therefrom. Among the strains obtained from IF03547, there should in turn be mentioned FV5069/pFV31 (EP-A-0 590 857, U.S. Pat. No. 5,518,906) and FV5069/pFV202 (WO 97/10340, U.S. Pat. No. 5,932,457). In the genus Corynebacterium the type *Corynebacterium glutamicum* should be mentioned in particular.

The aforementioned microorganisms may be cultivated continuously or discontinuously in a batch process or in a fed batch or repeated fed batch process in order to produce alkaline earth salts of D-pantothenic acid. A summary of known cultivation methods is described in the handbook by Chmiel (Bioprozesstechnik 1. Einführung in die Bioverfahrenstechnik [introduction to Biotechnology](Gustav Fischer Verlag, Stuttgart, 1991)) or in the handbook by Storhas (Bioreaktoren und periphere Einrichtungen (Vieweg Verlag, Brunswick/Wiesbaden, 1994)).

The culture medium to be used must suitably satisfy the requirements of the relevant microorganisms. Descriptions of culture media for various microorganisms are contained in the handbook "Manual of Methods for General Bacteriology" of the American Society for Bacteriology (Washington D.C., USA, 1981). Sugars and carbohydrates, for example glucose, sucrose, lactose, fructose, maltose, molasses, starch and cellulose, oils and fats such as soya bean oil, sunflower oil, groundnut oil and coconut oil, fatty acids, for example palmitic acid, stearic acid and linoleic acid, alcohols such as glycerol and ethanol, and also organic acids such as acetic acid may be used as sources of carbon. These substances may be used individually or as a mixture. Examples of nitrogen sources that may be used are organic nitrogen-containing compounds, such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources may be used individually or as a mixture. Phosphorus sources may be potassium dihydrogen phosphate or dipotassium hydrogen phosphate or the corresponding sodium-containing salts. The culture medium must also contain metal salts such as magnesium sulfate or iron sulfate that are necessary for growth. Finally, essential growth factors such as amino acids and vitamins may additionally be used together with the aforementioned substances. Precursors such as β-alanine or optionally their salts may furthermore be added to the culture medium. The aforementioned substances may be added to the culture in the form of a single addition or may be appropriately metered in during the cultivation.

Basic compounds such as ammonia or ammonia water or acidic compounds such as phosphoric acid or sulfuric acid may be used in an appropriate manner to control the pH of the culture, insofar as the process according to the invention does not involve any other measures. Anti-foaming agents such as fatty acid polyglycol esters may be used to control foam formation. Suitable selectively acting substances, for example antibiotics, may be added to maintain the stability of plasmids. Oxygen or oxygen-containing gas mixtures, for example air, are introduced into the culture in order to maintain aerobic conditions. The temperature of the culture is normally 20° C. to 50° C., and preferably 25° C. to 45° C. Cultivation is continued until a maximum amount of D-pantothenic acid has been formed. This objective is normally achieved within 10 hours to 160 hours.

It has been found that the alkaline earth salts, in particular the calcium salt and magnesium salt of D-pantothenic acid, can be produced in a simple manner by adding during the fermentation a solution or suspension of an alkaline earth-containing inorganic compound, such as for example calcium hydroxide or magnesium hydroxide, preferably calcium hydroxide or magnesium oxide, or also an alkaline earth salt of an organic acid, for example calcium acetate, calcium fumarate or calcium aspartate, continuously to the fermentation. It is also possible to meter in the alkaline earth-containing compound batchwise. In this way the cation necessary for forming the desired alkaline earth salt of D-pantothenic acid is introduced directly into the fermentation broth.

The fermentation process according to the invention is generally characterized in that a microorganism capable of producing D-pantothenic acid is first of all cultivated in a known manner using ammonia as pH regulator and nitrogen source, and in the following production stage the pH is preferably adjusted by using a solution or suspension of an alkaline earth-containing compound, for example calcium hydroxide, magnesium hydroxide, magnesium oxide, calcium acetate, calcium fumarate or calcium aspartate. If calcium salts of organic acids are used, the organic radicals are generally utilized as a carbon source by the microorganisms.

The solutions or suspensions of the alkaline earth-containing compounds that are used, in particular calcium hydroxide and magnesium hydroxide, have a concentration of 5–50 wt. %, preferably 5–30 wt. %, the range from 10–25 wt. % being most particularly preferred. It is also possible, according to the invention, to employ mixtures of various alkaline earth-containing compounds in these concentration ranges.

The alkaline earth compound is metered into the fermentation broth in such a way that the molar ratio of alkaline earth compound to the formed D-pantothenic acid is in the range 1:0.5 to 1:20, preferably in the range 1:1.3 to 1:10, more preferably in the range 1:1.3 to 1:2.5, the stoichiometric range from 1:1.8 to 1:2.2 being most particularly preferred. If necessary, the pH can be adjusted during the course of the fermentation by metering in ammonia in aqueous form or as a gas, should an excessive formation of byproducts containing carboxyl groups occur, in order to maintain the ratio of alkaline earth compound to formed D-pantothenic acid within the desired range.

The metering in of the alkaline earth compound may take place after a fermentation time of 1–70 hours, preferably 10–40 hours and most preferably 20–25 hours. The concentration of D-pantothenic acid at the start of the metering in of the alkaline earth compound is generally 0.5–70 g/liter, preferably 5–35 g/liter and particularly preferably 20–25 g/liter. The concentration of biomass at the time the alkaline earth compound is metered in is generally 1–30 g dry weight/liter, preferably 10–23 g dry weight/liter and particularly preferably 17–21 g dry weight/liter.

The invention also provides a process for producing powders or feed additives containing alkaline earth salts, in particular the calcium or magnesium salts of D-pantothenic acid, in a quick and cost-effective manner. To this end a fermentation broth prepared according to the process of the invention and containing in particular calcium or magnesium D-pantothenate is concentrated using known methods, for example with the aid of a rotary evaporator, thin-film evaporator or falling-film evaporator. The fermentation broth that has been concentrated in this way is then converted by spray drying or freeze drying techniques, such as are described for example in the handbook by M. L. Shuler and F. Kargi "Bioprocess Engineering, Basic Concepts" (Prentice Hall Inc., Englewood Cliffs, N.J., USA, 1992), or by other appropriate methods, into a preferably free-flowing powder or feed additive. A substance or preparation containing calcium or magnesium D-pantothenate may optionally be added at a suitable process stage in order to achieve a desired concentration level. The concentration of calcium or magnesium D-pantothenate—expressed as D-pantothenic acid—in the resultant product is 20 to 80 wt. %, preferably 30 to 75 wt. %. The product is suitable as a feed additive for use in animal nutrition.

The invention also provides a further method of producing powders or feed additives containing calcium or magnesium D-pantothenate. To this end a fermentation broth prepared as described above and containing, in particular, calcium or magnesium D-pantothenate is first freed either completely or partially from the biomass by known separation methods, for example centrifugation, filtration, decanting or a combination thereof. The cell-free fermentation broth is then concentrated using known methods, for example with the aid of a rotary evaporator, thin-film evaporator or falling-film evaporator. The suspension concentrated in this manner is then worked up by methods involving spray drying or freeze drying or by other suitable processes into a preferably free flowing powder. A substance or preparation containing calcium or magnesium D-pantothenate is optionally added at a suitable process stage in order to achieve a desired concentration value. The concentration of calcium or magnesium D-pantothenate, expressed as D-pantothenic acid, in the resultant product is 20 to 80 wt. %, preferably 30 to 75 wt. %. The product is suitable for use as a feed additive in animal nutrition.

The invention likewise provides a method for producing crystals containing calcium or magnesium D-pantothenate in a quick and cost-effective manner. To this end a fermentation broth prepared as described above and containing calcium or magnesium D-pantothenate is first of all freed as described above from the biomass. The cell-free fermentation broth is then concentrated using known methods, for example with the aid of a rotary evaporator, thin-film evaporator or falling-film evaporator. A hydrophilic, organic solvent, for example ethanol, methanol or acetone is then added to the suspension that has been concentrated in this way. Residual solid material is precipitated out by cooling the suspension to 0–8° C., preferably 0–5° C. The desired salt is then crystallized by inoculating with crystalline calcium or magnesium D-pantothenate or substances containing crystalline calcium or magnesium D-pantothenate. The crystallization takes place at 0–8° C., preferably 0–5° C., and lasts from 1 hour to 12 days, preferably 1 hour to 10 days, and particularly preferably 1 hour to 8 days. The crystalline crop obtained in this way is preferably washed with methanol and then dried. If a product of higher purity is required, the crystalline crop is taken up in a water-containing solution of methanol and is crystallized, optionally under the addition of activated charcoal. The water-containing solution of methanol has a methanol content of 70 to 99 vol. %, preferably 80 to 99 vol. %, and particularly preferably 90 to 99 vol. %.

The concentration of calcium or magnesium D-pantothenate in the crystalline product obtained in this way is 60 to 99 wt. %, preferably 70 to 99 wt. %, and particularly preferably 80 to 99 wt. %. The product is suitable for use as a feed additive in animal nutrition.

The concentration of D-pantothenic acid may be determined by known methods (Velisek; Chromatographic Science 60, 515–560 (1992)). Pure calcium D-pantothenate (>99 wt. %) has a content of 91.16 wt. % D-pantothenic acid. Pure magnesium D-pantothenate (>99 wt. %) has a content of 94.73 wt. % D-pantothenic acid.

EXAMPLES

The present invention is described in more detail hereinafter with the aid of examples of implementation.

For this purpose experiments were carried out with the strain *Escherichia coli* 5069/pFV31 producing D-pantothenic acid, which is registered as FERM-BP 4395 according to the Budapest Agreement at the Fermentation Research Institute, Agency of Industrial Science and Technology in 1-1-3, Higashi, Tsukuba-shi, Ibaraki (Japan)(U.S. Pat. No. 5,518,906).

Fermentation experiments were also carried out in which the calcium salt of fumaric acid or of aspartic acid was added to the fermentation broth in order to form calcium D-pantothenate directly.

DETAILED DESCRIPTION OF THE INVENTION

Example 1

Preparation of the calcium salt of D-pantothenate involving the metering in of a calcium hydroxide suspension 1. Preparation of the Inoculum (Master Cell Bank)

A sample of *Escherichia coli* FV5069/pFV31 was plated out on LBG agar that had been supplemented with 50 μg per ml ampicillin. This agar plate culture was incubated for 17 hours at 37° C. and then kept in a refrigerated cabinet at +4° C. Selected individual colonies were then propagated further in LBG broth. The LBG broth has the following composition: 10 g/liter peptone, 5 g/liter yeast extract, 5 g/liter NaCl and 1 g/liter glucose. LBG agar contains in addition 12 g/liter agar. Ready-for-use preparations may be obtained from Gibco/BRL (Paisley, Scotland, UK) as LB Broth Base or LB agar. The specified media are then obtained by adding 1 g/liter glucose. 10 ml cultures that had been obtained in 100 ml Erlenmeyer flasks were incubated for 16 hours at 37° C. and 180 rpm in an ESR incubator from Kuhner AG (Birsfelden, Switzerland). The cell suspension was then centrifuged off for 15 minutes at 4000 rpm in a J-6B centrifuge from Beckmann (Hanover, Germany). The cell pellet was resuspended in 10 ml of LBG medium that had been supplemented with 20% glycerol, was filled in 10 aliquots each of 1 ml under sterile conditions and frozen at −70° C. These cultures were used as master cell banks.

In order to prepare a working cell bank, LBG medium that had been supplemented with 50 µg/ml ampicillin was added in 10 ml portions to 100 ml Erlenmeyer flasks and then inoculated with 100 µl of the aforementioned master cell bank. The incubation was carried out for 16 hours at 37° C. and 180 rpm in an ESR incubator from Kuhner AG (Birsfelden, Switzerland).

After the incubation, the optical density (OD) of the culture suspension was determined with a LP2W photometer from the Dr. Lange Company (Berlin, Germany) at a measurement wavelength of 660 nm. The optical density was 3.5. The cell suspension was then added under sterile conditions to sterile 30 ml polyethylene test tubes from Greiner (Frickenhausen, Germany) and centrifuged at 2500 rpm for 15 minutes in a J-6B type centrifuge from Beckmann (Hanover, Germany). The separated biomass was resuspended in 10 ml of LBG medium that had been supplemented with 20% glycerol. The cell suspension was next added in 500 µl portions under sterile conditions to 1 ml sterile test tubes from Nalgene (New York, U.S.A.) and frozen at −70° C. The frozen cell suspensions prepared in this way were used as a working cell bank.

2. Preparation of a Fermentation Broth Containing Calcium D-pantothenate

In order to prepare a fermentation broth containing calcium D-pantothenate the working cell bank was first of all propagated in a shaking flask incubator and was then used to inoculate a preliminary fermenter. The culture from the preliminary fermenter was used to inoculate the production fermenter.

The SKA medium was used for the shaking flask culture (Table 1). The SKA medium was prepared as follows: 7.0 g $(NH_4)_2SO_4$, 0.5 g $KH_2PO_4$, 1.0 g $K_2HPO_4$, 0.5 g $MgSO_4 \cdot 7H_2O$, 0.01 g $MnSO_4 \cdot H_2O$, 0.01 g $ZnSO_4 \cdot 7H_2O$, 0.005 g $Fe_2(SO_4)_3$, 0.7 g STRUCTOL anti-foaming agent (Schill & Seilacher GmbH & Co., Hamburg, Germany) and 20 g corn steep liquor that had previously been adjusted to pH 6.8 with 25% ammonia solution were weighed out into a 1 liter beaker, which was then made up to 825 g with distilled water. This salt solution containing corn steep liquor was sterilized in an autoclave for 20 minutes at 121° C. A solution consisting of 24 g of glucose and 0.002 g of thiamine HCl, which had been made up to 125 g with distilled water, was sterilized by filtration. 10 g $CaCO_3$ were weighed into a 100 ml flask and sterilized in an autoclave for 20 minutes at 123° C. The SKA medium was obtained by combining the two aforementioned components with the salt solution containing the corn steep liquor.

This SKA medium was added in 12.5 ml portions to 100 ml Erlenmeyer flasks and then inoculated with 0.5 ml of a cell suspension. A frozen sample of the working cell culture that had been diluted 1:100 with sterile physiological saline was used as cell suspension. The incubation was carried out for 20 hours at 32° C. and 150 rpm in a RC-1-TK incubator from Infors AG (Bottmingen, Switzerland). The optical density subsequently determined at a measurement wavelength of 660 nm (OD 660) was 12.5.

In order to inoculate 20 kg of the pre-culture medium A1-102 that had been obtained in a 42 liter capacity stirred reactor fermenter from Bioengineering (Wald, Switzerland, LP-42 Model), 0.5 ml of the SKA mediums was diluted 1:100 and 50 ml of the resulting suspension were added to the fermenter. The pre-culture medium A1-102 contained the constituents listed in Table 2. The culture was cultivated for 15.5 hours at a temperature of 37° C., a volume-specific aeration of 0.5 vvm, an oxygen partial pressure of 20% of the atmospheric saturation, and a pH of 6.5 until an OD660 of 11.3 had been 35 reached.

For the inoculation of 5830 g of the principal culture medium M1-425 that had been obtained in 14 liter capacity stirred reactor fermenters from B.Braun (BBI, Germany, Melsungen, Biostat E/ED Model), 423 ml of the second pre-culture were added to the medium A1-102. The principal culture medium M1-425 contained the constituents listed in Table 3. The culture was first of all cultivated for 6.5 hours at a temperature of 37° C., a volume-specific aeration of 0.75 vvm, a minimum stirring rate of 400 rpm, a pH of 6.5 until an OD660 of 18.6 had been reached, and an oxygen partial pressure of 2% of atmospheric saturation. The culture was then cultivated for a further 41 hours at a temperature of 37° C., an oxygen partial pressure of 2% of atmospheric saturation and a pH 6.0, until an OD660 of 66.8 had been reached. After a fermentation time of 13 hours β-alanine was added in a concentration of 152.7 g in 570 ml $H_2O$ over a period of 34.5 hours. After a fermentation time of 21.5 hours, a 10% $Ca(OH)_2$ solution was added over a period of 26 hours in order to stabilize the pH. 3.43 kg of the M2-257 medium having a glucose concentration of 650.8 g/liter and a thiamine HCl concentration of 35.7 mg/liter were metered in within 41 hours.

The optical density (OD) was then determined with a LP1W type digital photometer from Dr. Bruno Lange GmbH (Berlin, Germany) at a measurement wavelength of 660 nm, and the concentration of formed D-pantothenic acid was determined by means of HPLC (Hypersil APS 2 5 µm, 250×5 mm, RI detection).

A calcium D-pantothenate concentration of 49.8 g/liter measured as D-pantothenic acid was determined in the fermentation sample after 47.5 hours.

TABLE 1

Composition of the SKA Medium

| Component | Concentration (per liter) |
|---|---|
| Glucose | 24 g |
| Corn Steep Liquor | 20 g |
| $(NH_4)_2SO_4$ | 7 g |
| $KH_2PO_4$ | 0.5 g |
| $K_2HPO_4$ | 1 g |
| $MgSO_4 \cdot 7H_2O$ | 0.5 g |
| $FeSO_4 \cdot 7H_2O$ | 5 mg |
| $MnSO_4 \cdot H_2O$ | 10 mg |
| $ZnSO_4 \cdot 7H_2O$ | 10 mg |
| $CaCO_3$ | 10 g |
| Thiamine.HCl | 2 mg |
| Structol | 0.7 g |

TABLE 2

Composition of the A1-102 Medium

| Component | Concentration (per liter) |
|---|---|
| Glucose | 24 g |
| Corn Steep Liquor | 20 g |
| $(NH_4)_2SO_4$ | 7 g |
| $KH_2PO_4$ | 0.5 g |
| $K_2HPO_4$ | 1 g |
| $MgSO_4 \cdot 7H_2O$ | 0.5 g |
| $FeSO_4 \cdot 7H_2O$ | 10 mg |
| $MnSO_4 \cdot H_2O$ | 10 mg |
| Thiamine HCl | 3 mg |
| Structol | 0.6 g |

TABLE 3

Composition of the M1-425 Medium

| Component | Concentration (per liter) |
|---|---|
| Glucose | 18 g |
| Corn Steep Liquor | 40 g |
| β-Alanine | 15 g |
| $NH_4Cl$ | 6.8 g |
| $(NH_4)_2SO_4$ | 3.3 g |
| $KH_2PO_4$ | 0.6 g |
| $K_2HPO_4$ | 1.2 g |
| $MgSO_4 \cdot 7H_2O$ | 0.67 g |
| $MnSO_4 \cdot H_2O$ | 10 mg |
| Thiamine.HCl | 1.6 mg |
| Structol | 0.6 g |

Example 2

Preparation of the Calcium Salt of D-pantothenic Acid Involving the Metering in of a Calcium Acetate Solution The *Escherichia coli* strain FV5069/pFV31 was cultivated in the SKA shaking flask medium as described in Example 1 (Table 1). The suspension was then diluted 1:100 and 17.5 ml of the suspension in this dilution was used to inoculate 7 kg of A1-102 medium (Table 2) in a 14 liter capacity stirred reactor fermenter (BBI, Germany, Melsungen, Biostat E Model).

The culture was cultivated for 15.5 hours at a temperature of 37° C., a volume-specific aeration of 0.5 vvm, an oxygen partial pressure of 20% of atmospheric saturation and a pH of 6.5 until an OD660 of 11.6 had been reached.

After inoculation in the production fermenter (14 liter stirred reactor fermenter, BBI, Germany, Melsungen, Biostat ED Model) the same cultivation conditions as described in Example 1 were established. A 25 wt. % solution of calcium acetate was used to adjust the pH. The replacement of ammonia water by calcium acetate was complete after 24 hours. The overall process time of the fermentation was 52 hours. The metering in of 3.4 kg of M2 medium was effected within a period of 40 hours. At the end of the fermentation a: calcium D-pantothenate concentration of 43.7 g/liter, measured as D-pantothenic acid, was determined.

Example 3

Preparation of a Product Containing Calcium D-pantothenate 1.0 liter of the fermentation broth prepared according to the method described in Example 1 and containing calcium D-pantothenate was first of all evaporated in vacuo at 60° C. in a rotary evaporator (Buchi Rotavapor RE-120 laboratory rotary evaporator, Büchi-Labortechnik GmbH, Constance, Germany) to reduce the liquid fraction to about 50% dry content. The broth concentrated in this way was then spray dried to obtain the calcium salt of pantothenic acid (Büchi-190 laboratory spray dryer, inlet temperature 107° C., outlet temperature 78° C., −40 mbar, 600 NL/h, Büchi-Labortechnik GmbH, Constance, Germany).

The product prepared in this way had a content of calcium D-pantothenate of 42 wt. % measured as D-pantothenic acid.

Example 4

Preparation of a Biomass-Free Product Containing Calcium D-pantothenate

The biomass was first of all separated by centrifugation (Biofuge-Stratos laboratory centrifuge, Heraeus, Dusseldorf, Germany; 20 minutes, 4,000 rpm) in 1.01 of the calcium D-pantothenate-containing fermentation broth prepared according to the method described in Example 1. The broth treated in this way was then processed in vacuo at 60° C. in a rotary evaporator (Büchi Rotavapor RE-120 laboratory rotary evaporator, Büchi-Labortechnik GmbH, Constance, Germany) to reduce the liquid fraction to about 50% dry content. The broth concentrated in this way was then spray dried to form the calcium salt of pantothenic acid (Büchi-190 laboratory spray dryer, inlet temperature 107GC, outlet temperature 78° C., 40 mbar, 600 NL/h, Büchi-Labortechnik GmbH, Constance, Germany).

The product prepared as described above had a content of calcium D-pantothenate of 64 wt. %, measured as pantothenic acid.

Example 5

Preparation of Crystalline Calcium D-pantothenate 3,600 g of the fermentation broth prepared according to Example 1 and containing calcium D-pantothenate were separated from the biomass by filtration and the resultant filtrate was reduced to 700 g by evaporation at 60° C. in a rotary evaporator (Büchi Rotavapor RE-1 51 laboratory rotary evaporator, Büchi-Labortechnik GmbH, Constance, Germany). The residue was then taken up and dissolved in 3,200 g of methanol. After cooling the solution to room temperature the insoluble constituents were separated by centrifugation (Biofuge-Stratos laboratory centrifuge, Heraeus, Dusseldorf, Germany; 20 minutes, 4,000 rpm). The supernatant clarified in this way was concentrated to dryness once more in a rotary evaporator and the residue was taken up again in 950 g of methanol. After cooling to a temperature of 2° C. the crystallization of the calcium salt of pantothenic acid from the concentrated solution thereby obtained was started by inoculation with 2.5 g of crystalline calcium D-pantothenate.

After separating the organic phase in vacuo a crystalline product was obtained having a content of calcium D-pantothenate of 84 wt. %.

In a further recrystallization step the concentration was successfully increased to 96 wt. %.

Example 6

Preparation of the Magnesium Salt of D-pantothenic Acid Involving the Metering in of a magnesium hydroxide suspension The preparation of the inoculum for the primary culture was carried out as described in Example 1. For the inoculation of 5830 g of the primary culture medium M1-425 that had been obtained in 14 liter capacity stirred reactor fermenters from B.Braun (BBI, Germany, Melsungen, Biostat E/ED Model), 846 ml of the second pre-culture in medium A1-102 were added. The primary culture medium M1-425 contained the constituents listed in Table 3. The culture was first of all cultivated for 6.5 hours at a temperature of 37° C., a volume-specific aeration of 0.75 vvm, a minimal stirring rate of 400 rpm and a pH of 6.5 until an OD660 of 22.0 had been reached, and an oxygen partial pressure of 2% of atmospheric saturation. The culture was then cultivated for a further 48 hours at a temperature of 37° C., an oxygen partial pressure of 2% of atmospheric saturation, and a pH of 6.0 until an OD660 of 67.6 had been reached. After a fermentation time of 23.0 hours, a 15% $Mg(OH)_2$ suspension was metered in over a period of 31.5 hours to stabilize the pH. 4.28 kg of the medium M2-261 having a glucose concentration of 584.7 g/liter, a β-alanine concentration of 50.7 g/liter and a thiamine HCl concentration of 35.7 mg/liter were metered in within 48 hours.

The optical density (OD) was then measured with an LP1W type digital photometer from Dr. Bruno Lange GmbH (Berlin, Germany) at a measurement wavelength of 660 nm and the concentration of formed D-pantothenic acid was determined by means of HPLC(Hypersil APS 2 5 μm, 250×5 mm, RI-Detection).

A magnesium D-pantothenate concentration of 48.2 g/liter measured as D-pantothenic acid was determined in the fermentation end sample after 54.5 hours.

What is claimed is:

1. A process for preparing one or more alkaline earth salts of D-pantothenic acid or mixtures containing one or more alkaline earth salts of D-pantothenic acid, from fermentation broths, comprising:
   a) fermenting a microorganism that produces D-pantothenic acid in a fermentation broth wherein one or more alkaline earth compounds selected from the group consisting of calcium oxide, calcium hydroxide, magnesium hydroxide, magnesium oxide and an alkaline earth salt of an organic acid is added to the fermentation broth after 1 to 70 hours of fermentation time have elapsed;
   b) optionally removing all or a portion of the biomass after fermentation is complete;
   c) concentrating the fermentation broth; and
   d) obtaining one or more alkaline earth salts of D-pantothenic acid in pure form or as a mixture containing constituents of the fermentation broth.

2. Process according to claim 1, wherein the one or more alkaline earth compounds are added when the concentration of D-pantothenic acid is from 0.5 to 70 g/liter.

3. The process according to claim 2, wherein the one or more alkaline earth compounds are added when the concentration of D-pantothenic acid is from 5 to 35 g/liter.

4. The process according to claim 1, wherein the one or more alkaline earth compounds are added to the fermentation broth in a molar ratio of 1:0.5 to 1:20, relative to D-pantothenic acid.

5. The process according to claim 4, wherein the one or more alkaline earth compounds are added to the fermentation broth in a molar ratio of 1:1.3 to 1:10, relative to D-pantothenic acid.

6. The processing according to claim 4, wherein one or more alkaline earth compounds are added to the fermentation broth in a batchwise or continuous fashion.

7. The process according to claim 1, further comprising adding a calcium salt of the organic acid.

8. The process according to claim 7, wherein the organic acid is selected from the group consisting of fumaric acid and aspartic acid.

9. The process according to claim 1, further comprising
   a) separating the biomass from the fermentation broth containing the alkaline earth salts of D-pantothenic acid to obtain a cell-free fermentation broth;
   b) concentrating the cell-free fermentation broth;
   c) adding a hydrophilic organic solvent to concentrate obtained in b); and then
   d) crystallizing the alkaline earth salts of pantothenic acid and optionally further purifying the salts.

* * * * *